(12) United States Patent
Hennessy

(10) Patent No.: US 9,005,164 B2
(45) Date of Patent: Apr. 14, 2015

(54) LOW-PROFILE ONE-WAY VALVE

(75) Inventor: Eric R. Hennessy, Lewisville, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 33 days.

(21) Appl. No.: 12/966,504

(22) Filed: Dec. 13, 2010

(65) Prior Publication Data
US 2011/0313354 A1 Dec. 22, 2011

Related U.S. Application Data

(60) Provisional application No. 61/286,661, filed on Dec. 15, 2009.

(51) Int. Cl.
| | |
|---|---|
| *A61M 29/00* | (2006.01) |
| *A61B 1/00* | (2006.01) |
| *A61M 25/10* | (2013.01) |
| *A61M 39/24* | (2006.01) |
| *A61B 17/34* | (2006.01) |

(52) U.S. Cl.
CPC ........ *A61B 1/00082* (2013.01); *A61M 25/1018* (2013.01); *A61M 2039/2433* (2013.01); *A61B 2017/3441* (2013.01); *A61M 39/24* (2013.01); *A61M 2039/2426* (2013.01)

(58) Field of Classification Search
CPC ................... A61B 1/00082; A61B 2017/3441; A61M 39/24; A61M 2039/2426; A61M 2039/267; A61M 25/1018; A61M 25/1025; A61M 2039/2433

USPC ........................ 604/167.03, 43, 99.01–99.04, 604/167.01–167.06, 246, 247, 250, 99.02; 606/194

See application file for complete search history.

(56) References Cited

U.S. PATENT DOCUMENTS

| | | | | |
|---|---|---|---|---|
| 3,477,438 | A * | 11/1969 | Allen et al. ................. | 604/99.03 |
| 4,038,983 | A * | 8/1977 | Mittleman et al. ............ | 604/124 |
| 4,106,497 | A | 8/1978 | Percarpio | |
| 4,337,770 | A * | 7/1982 | Young et al. ..................... | 604/30 |
| 4,795,426 | A * | 1/1989 | Jones ............................. | 604/539 |
| 5,224,933 | A | 7/1993 | Bromander | |
| 5,643,227 | A * | 7/1997 | Stevens ......................... | 604/264 |
| 5,853,397 | A * | 12/1998 | Shemesh et al. .............. | 604/247 |
| 6,595,950 | B1 * | 7/2003 | Miles et al. ..................... | 604/80 |
| 2005/0171488 | A1 * | 8/2005 | Weaver et al. ................ | 604/247 |
| 2012/0010646 | A1 * | 1/2012 | Keith et al. .................... | 606/196 |

FOREIGN PATENT DOCUMENTS

| | | |
|---|---|---|
| JP | 2006-087747 A | 4/2006 |
| JP | 2006-102222 A | 4/2006 |

OTHER PUBLICATIONS

PCT International Search Report and Written Opinion of the International Searching Authority; May 6, 2011; 12p.

* cited by examiner

*Primary Examiner* — Theodore Stigell
(74) *Attorney, Agent, or Firm* — Brinks Gilson & Lione

(57) ABSTRACT

A valve configured for a lumen of medical device is provided. The valve includes a valve body that may be elastically deformed from a first configuration to a second configuration. The valve body includes a lumen having a closed configuration and an open configuration. The lumen may be actuated from the closed configuration to the open configuration by elastically deforming the valve body from the first configuration to the second configuration. The valve body may include a portion configured to form a seal with an interior surface of a lumen of a medical device.

16 Claims, 14 Drawing Sheets

LOW-PROFILE ONE-WAY VALVE

RELATED APPLICATION

The present application claims the benefit of U.S. Provisional Application No. 61/286,661, filed on Dec. 15, 2009, the entirety of which is hereby incorporated by reference.

TECHNICAL FIELD

The present disclosure relates generally to medical devices, and more particularly to a low-profile one-way valve configured for use with a medical device.

BACKGROUND

Conventional surgical procedures for pathologies and/or trauma located deep within the body can cause significant trauma to intervening tissues. Open surgical procedures often require a long incision, extensive muscle stripping, prolonged retraction of tissues, denervation, and devascularization of tissue in order to access a surgical site. Most of these surgeries require several hours of recovery room time and several weeks of post-operative recovery time due to the use of general anesthesia and the destruction of tissue during the surgical procedure. In some cases, these invasive procedures lead to permanent scarring and pain.

Minimally invasive alternatives, such as endoscopic techniques, reduce pain, post-operative recovery time, and the destruction of healthy tissue. In minimally invasive surgery, the site of pathology is accessed through portals rather than through a significant incision, thus preserving the integrity of intervening tissues. These minimally invasive techniques also often require only local anesthesia. The avoidance of general anesthesia can reduce post-operative recovery time and the risk of complications.

Nevertheless, there still exists a need for the development of devices and methods to improve minimally invasive surgical techniques. For example, some endoscopic procedures, such as peroral cholangioscopy, suffer procedural inefficiency due to limitations in currently available medical devices. Peroral cholangioscopy is usually performed by two experienced endoscopists using a "mother-baby" scope system, in which a thin fiberscope is inserted into the working channel of a large therapeutic endoscope (e.g., a duodenoscope). The mother-baby scope technique can be expensive with regard to personnel and equipment: two endoscopists plus assistants, two image processors (one for each camera), and expensive fiber optics in the baby scope that can often be damaged during standard manipulation with resulting image degradation. The standard 1.2 mm working channel of fiber optic baby scopes limits diagnostic and therapeutic options. It is therefore desirable to provide an endoscope configured to function as a cholangioscope by being dimensioned to be navigable through hepatic and pancreatic ducts. Such scopes are currently available, but they encounter problems of efficient introduction to a patient's biliary duct in a procedure that provides high quality images (e.g., superior to fiber optics imaging) at a desirable procedure cost. These problems include the difficulty of navigating a larger fiber optic baby scope having a greater than 1.2 mm working channel through a mother scope and into a patient's biliary duct. If one is to introduce a small scope (along the size of a "baby scope" or smaller) into the biliary ducts or other patient body structure without a primary (e.g., "mother") scope, it is necessary to provide some type of "navigating track" because the smaller scopes are not sufficiently rigid/robust to be directed/navigated independently and directly through the esophagus, stomach, and duodenum to, for example, the common bile duct.

Accordingly, techniques are being developed to conduct direct peroral cholangioscopy (POC). Direct POC requires only a single endoscopist working with a single image processor, using a CMOS or CCD camera system that provides a 2 mm accessory channel, and that can be used with existing scopes, image processors, and monitors. One example of such improved technology is disclosed in "Overtube-balloon-assisted direct peroral cholangioscopy by using an ultra-slim upper endoscope" (Choi et al., Gastrointestinal Endoscopy, 69(4):935-40, April 2009), where an over-tube with a balloon of the type used for double-balloon enteroscopy was directed into the duodenum adjacent the Ampulla of Vater with an ultra-slim scope supported in the lumen of the over-tube, whereafter the scope was directed into the previously-dilated bile duct.

It would be advantageous to provide devices for more efficient minimally invasive procedures. In particular, it would be advantageous to provide devices for efficient introduction of an ultra-slim scope suitable for cholangioscopy and pancreatoscopy in conjunction with use of a standard-sized endoscope (e.g., duodenscope) that can be exchanged out without significant loss of procedural efficiency, but without limiting the equipment and/or procedure to a mother-baby scope configuration, and also providing for easier, more efficient navigation into the bile duct or other locations.

SUMMARY

The present disclosure generally provides a valve configured for a lumen of a medical device. The valve may be placed in a proximal end of an inflation lumen and used to seal the lumen, and allow introduction or release of fluid or gas as desired. The valve may be used, for example, with a balloon catheter in an endoscopic procedure to facilitate an exchange of endoscopes over the catheter shaft.

In one embodiment, the valve includes a valve body having a first segment and a second segment. The second segment is elastically deformable from a first configuration to a second configuration. The first segment is integral with the second segment. A lumen extends through the valve body. The lumen includes a first portion extending through the first segment and a second portion extending through the second segment. The second portion is actuable between an open configuration and a closed configuration. Elastic deformation of the second segment from the first configuration to the second configuration causes the second portion to actuate from the closed configuration to the open configuration.

In another embodiment, the valve includes an elastically deformable body extending from a proximal end to a distal end along a longitudinal axis. A slit extends through the body from the proximal end to the distal end along the longitudinal axis. The body includes a first radial axis corresponding to the slit. Compression of the body along the first radial axis may cause elastic deformation of the body and may cause the slit to open to provide a path of fluid communication through the body from the proximal end to the distal end. Optionally, the valve may further comprise a seal portion proximal to and integral with the body. The seal portion includes a lumen extending longitudinally therethrough, and preferably is aligned with the slit such that a path of fluid communication exists through the body and the seal portion when the slit is open. The seal portion is configured to engage and form a fluid tight seal with an interior surface of an inflation lumen of an elongate medical device, such as a balloon catheter.

In another aspect, a balloon catheter assembly is provided. In one embodiment, the balloon catheter assembly includes a balloon catheter having a proximal end, a distal end, an inflation lumen extending from the proximal end to the distal end, and a balloon disposed on the distal end and in fluid communication with the inflation lumen. The balloon catheter assembly further includes a valve comprising a valve body having a collapsed lumen extending therethrough. The collapsed lumen can be opened by elastically deforming the valve body from a first configuration to a second configuration. The balloon catheter assembly further includes a detachable hub comprising a seal capable of elastically deforming the valve body. Optionally, the valve further comprises a seal portion proximal to and integral with the valve body, the seal portion comprising a lumen extending therethrough, wherein the seal portion lumen and the collapsed lumen are aligned and wherein the seal portion is configured to engage and form a fluid tight seal with an interior surface of the inflation lumen of the balloon catheter.

In another aspect, a method of exchanging devices over a balloon catheter is provided. In one embodiment, the method includes advancing a first medical device to a target area. A balloon catheter is advanced through the first medical device to the target area. The balloon catheter includes a distally located balloon, an inflation lumen in fluid communication with the balloon, and a valve disposed in the inflation lumen. The valve includes a valve body having a first segment and a second segment, the second segment elastically deformable from a first configuration to a second configuration. The first segment is integral with the second segment. A valve lumen extends through the valve body. The valve lumen includes a first portion extending through the first segment and a second portion extending through the second segment. The second portion is actuable between an open configuration and a closed configuration. Elastic deformation of the second segment from the first configuration to the second configuration causes the second portion to actuate from the closed configuration to the open configuration. The method further includes anchoring the balloon catheter at the target area by opening the valve and introducing an inflation media through the valve lumen and the inflation lumen to the balloon, thereby inflating the balloon. The valve may then be closed. Optionally, the valve may be opened and closed with use of a Tuohy-Borst seal. The first medical device is removed from the target area by advancing the first medical device in a proximal direction over the balloon catheter until the balloon catheter is no longer disposed through the first medical device. A second medical device may then be advanced over the balloon catheter to the target area.

Other devices, systems, methods, features and advantages will be, or will become, apparent to one with skill in the art upon examination of the following figures and detailed description. It is intended that all such additional devices, systems, methods, features and advantages be included within this description, and be protected by the following claims.

BRIEF DESCRIPTION OF THE DRAWINGS

The system may be better understood with reference to the following drawings and description. The components in the figures are not necessarily to scale, with emphasis instead being placed upon illustrating the principles of the present disclosure. Moreover, in the figures, like referenced numerals designate corresponding parts throughout the different views.

DETAILED DESCRIPTION

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The present disclosure also contemplates other embodiments "comprising," "consisting of" and "consisting essentially of," the embodiments or elements presented herein, whether explicitly set forth or not.

The term "proximal," as used herein, refers to a direction that is generally toward a physician during a medical procedure.

The term "distal," as used herein, refers to a direction that is generally toward a target site within a patient's anatomy during a medical procedure.

The term "hub," as used herein, refers to the proximal end structure of a balloon catheter including a connection structure configured for effective connection to provide a path of fluid communication between a source of inflation fluid or gas, a catheter inflation lumen, and a balloon lumen, and includes manifold-style hubs that may have more complex or ancillary structures.

The term "Tuohy-Borst seal," as used herein, refers to the specific structure associated in the art with that name, as well as all equivalent simple seals configured for maintaining fluid-patency during introduction of a solid item through a seal.

The term "ultra-slim endoscope," as used herein, refers to an endoscope having an outer diameter of about 6.0 mm or less.

The term "frustum," as used herein, refers to the portion of a solid that lies between two parallel planes intersecting the solid.

Devices and Systems

Figure 1:
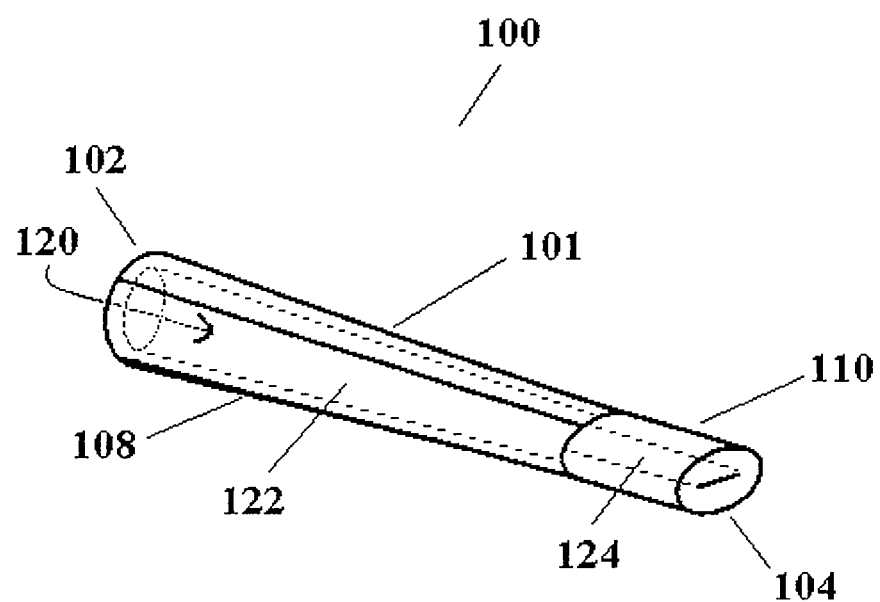
FIG. 1 depicts a perspective view of a valve configured for a medical device.

FIG. 1 depicts a perspective view of valve 100 in a closed configuration. The valve includes a valve body 101 having a proximal end 102, a distal end 104, and a lumen 120 extending from the proximal end to the distal end. The valve body includes a first segment 108 integral with a second segment 110. The second segment is elastically deformable from a first, relaxed configuration to a second, deformed configuration. Lumen 120 includes a first portion 122 extending through segment 108, and a second portion 124 extending through segment 110. The second portion has a closed configuration and an open configuration. When valve 100 is in the closed configuration, segment 110 is in the first configuration and portion 124 is in a closed (i.e., collapsed) configuration. As will be described in greater detail below, when segment 110 is elastically deformed to the second configuration, portion 124 opens to provide a path of fluid communication through lumen 120 from proximal end 102 to distal end 104.

Figure 2:
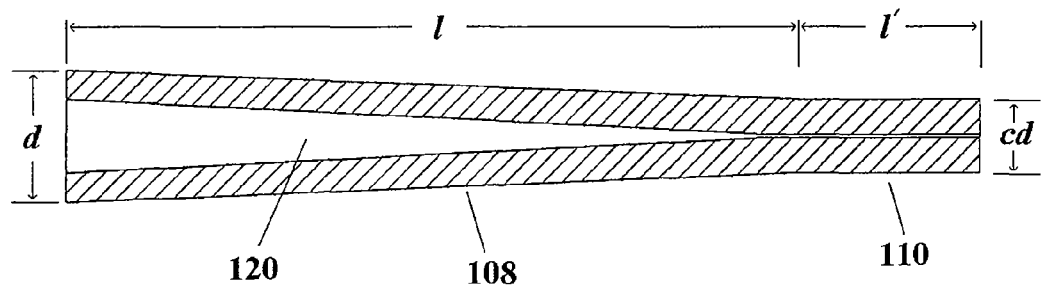
FIG. 2 depicts a side longitudinal cross sectional view of the valve of FIG. 1.
Figure 3:
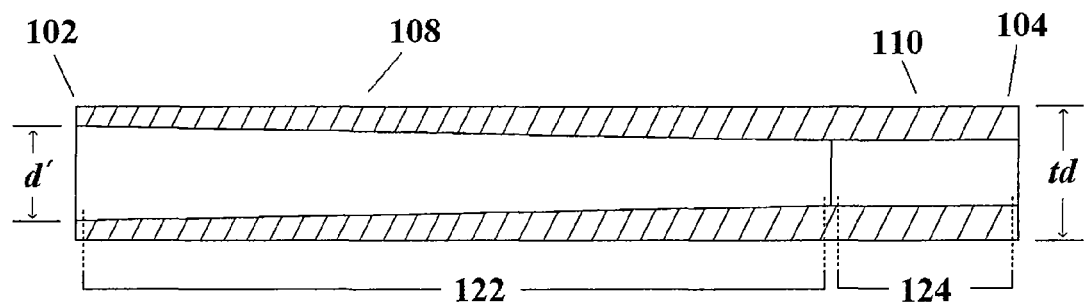
FIG. 3 depicts a top longitudinal cross sectional view of the valve of FIG. 1.
Figure 4:
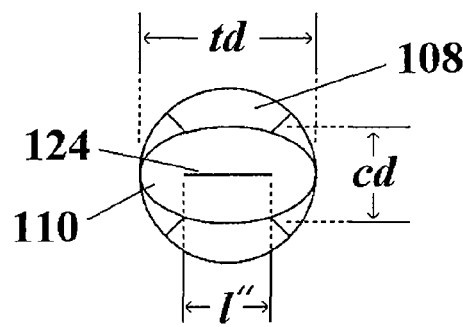
FIG. 4 depicts an end view of the valve of FIG. 1.

FIGS. 2-3 depict side and top longitudinal cross sectional views of valve 100, respectively, and FIG. 4 depicts an end view of the valve. As depicted, segment 108 has a frustum shaped body, and segment 110 has an elliptic cylinder shaped body. Preferably, segment 108 has a circular cross section at proximal end 102 that tapers to an elliptic shaped cross section moving toward segment 110. Segment 108 generally has a length l of about 1 mm to about 25 mm, and segment 110 generally has a length l' of about 0 mm to about 3 mm. Thus, valve body 101 generally has a length of about 1 mm to about 28 mm. Segment 108 has a circular cross section diameter d at proximal end 102, generally ranging from about 0.5 mm to about 3 mm. Segment 110 has an elliptic or oval shaped cross section, defined by a transverse diameter td and a conjugate diameter cd. The transverse diameter generally ranges from about 0.5 mm to about 3.5 mm, and the conjugate diameter generally ranges from about 0.25 mm to about 3.5 mm. At the intersection of segments 108 and 110 (i.e., at the distal end of segment 108 near the proximal end of segment 110), segment 108 has an elliptic cross section with transverse and conjugate diameters the same or about the same as the respective transverse and conjugate diameters of segment 110.

The length of lumen 120 is defined by the additive length of segments 108 and 110 (i.e., l+l'). First portion 122 of lumen 120 may have a circular cross-section at proximal end 102 with a diameter d' ranging from about 0.1 mm to about 2.5 mm. The diameter of first portion 122 decreases as the lumen narrows moving toward segment 110, as depicted in FIGS. 2-3. Second portion 124 is generally flat (e.g., appears as a slit) when in the collapsed configuration, having a transverse length l" along transverse diameter td ranging from about 0.4 mm to about 3.4 mm. While particular dimensions have been described, the skilled artisan will appreciate that all dimensions provided herein are intended as examples only, and that the presently disclosed valve may be fabricated having different dimensions and shapes as appropriate for the intended application.

Figure 5:
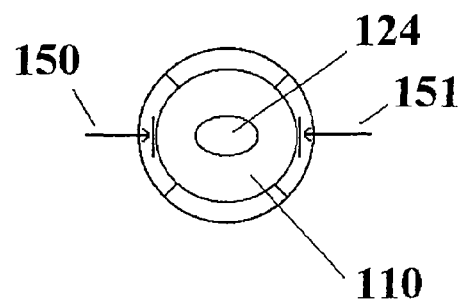
FIG. 5 depicts an end view of the valve of FIG. 1.

FIG. 5 shows an end view of valve 100 in an open configuration where segment 110 is in the second configuration. Arrows 150 and 151 represent two opposing forces applied to the external surface of segment 110 along transverse diameter td. As the transverse diameter decreases and the conjugate diameter cd increases, second portion 124 opens to provide a path of fluid communication through lumen 120 from proximal end 102 to distal end 104, such as depicted in FIG. 5. The valve may be closed by allowing segment 110 to relax back to the first configuration.

Figure 6:
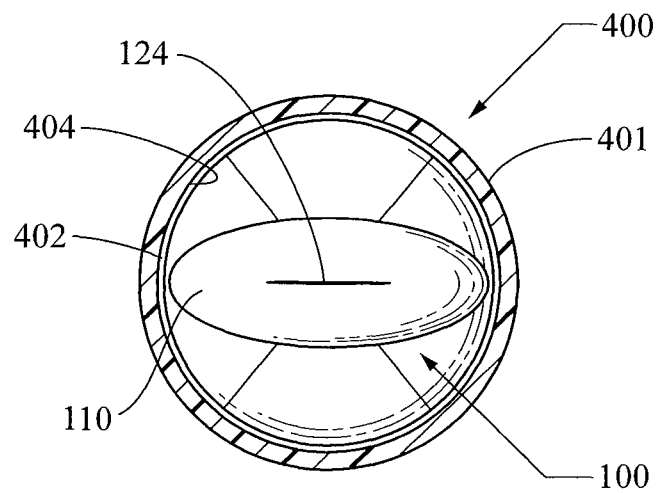
FIGS. 6-8 depict a cross sectional view of a catheter lumen having the valve of FIG. 1 disposed therein.
Figure 7:
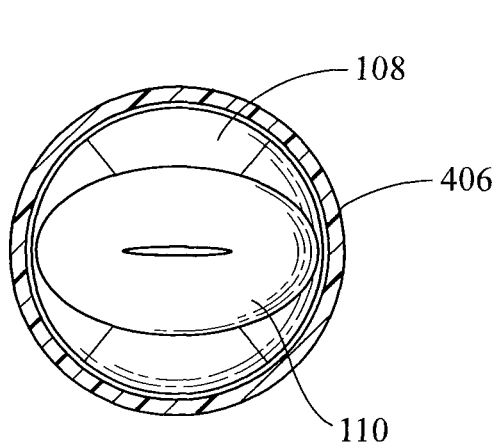
Figure 8:
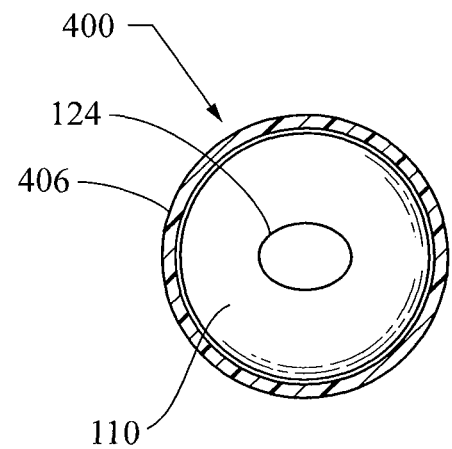

In one exemplary embodiment, the valve can be configured for use with a balloon catheter. The valve may be fabricated with appropriate dimensions, and thereafter press fit or glued into the catheter lumen at the proximal end of the catheter shaft. The valve may be configured to be placed in the absolute proximal end of the catheter lumen, or alternatively, may be configured for placement in a location slightly distal from the proximal end. FIGS. 6-8 depict a transverse cross-sectional view of a catheter shaft 401 of a balloon catheter 400 wherein valve 100 is disposed within an inflation lumen 402. Preferably, proximal end 102 is in intimate contact with the inner lumen surface 404, thereby forming a fluid tight seal therewith. The seal impedes flow of fluid or gas in the proximal and distal directions around the valve outer diameter. FIG. 6 shows valve 100 in the closed configuration. FIG. 7 shows valve 100 in a partially open configuration, there being an external force applied to the external surface 406 of catheter shaft 401, causing reduction of the catheter outer and inner diameters, as well as segment 110 along transverse diameter td. FIG. 8 shows valve 100 in the open configuration, the external force applied to the external surface 406 having deformed segment 110 such that transverse diameter td and conjugate diameter cd are the same, or about the same. With the valve in a partially open or open configuration, a fluid or gas may be introduced through lumen 120 in either a distal or proximal direction, as desired. A Tuohy-Borst seal may be used to apply the external force to elastically deform valve 100 from a closed configuration to an open configuration. For example, a Tuohy-Borst seal may be tightened down on the catheter shaft external surface 406 until valve 100 is in a desired open configuration, such as depicted in FIG. 8 (Tuohy-Borst seal not shown).

Optionally, a fluid may be introduced through the valve in a distal direction even when the valve is closed. The shape of lumen 120 through first portion 122 is configured to allow sufficient fluid pressure to be applied through first portion 122 such that second portion 124 opens in response, allowing fluid introduction in a distal direction. However, it is to be understood that when the valve is closed (i.e., when portion 124 is collapsed), fluid movement through second portion 124 is generally prevented or substantially impeded, particularly backflow therethrough (i.e., fluid movement in the proximal direction).

In another exemplary embodiment, valve 100 may be used with a balloon catheter having a detachable hub. Some balloon catheters have hubs that are fixedly and irremovably attached to the catheter shaft. The outer diameter and/or cross-sectional area of these hubs are such that they would not fit through an elongate surgical device such as, for example, a lumen of a large-bore catheter, polymer biliary stent, working/accessory channel of an endoscope or other minimally invasive image-capture device. Thus, to perform an exchange over such a catheter without loss of fluid patency in the balloon, one must first tie off or otherwise seal the catheter lumen to maintain fluid patency, and thereafter cut the hub from the catheter shaft. By using valve 100 in combination with a balloon catheter having a detachable hub, an elongate surgical device (e.g., duodenoscope, ultra-slim endoscope, other camera or image-capturing device, polymer stent, larger-bore catheter, etc.) may be passed over the entire length of the catheter shaft without impediment at the proximal end of the catheter, and without irreversibly removing the hub from the catheter shaft. Further, because valve 100 fits within the lumen of the balloon catheter, the valve attributes no additional outer diameter to the catheter shaft, and an endoscope or other device can be smoothly exchanged thereover.

Figure 9:
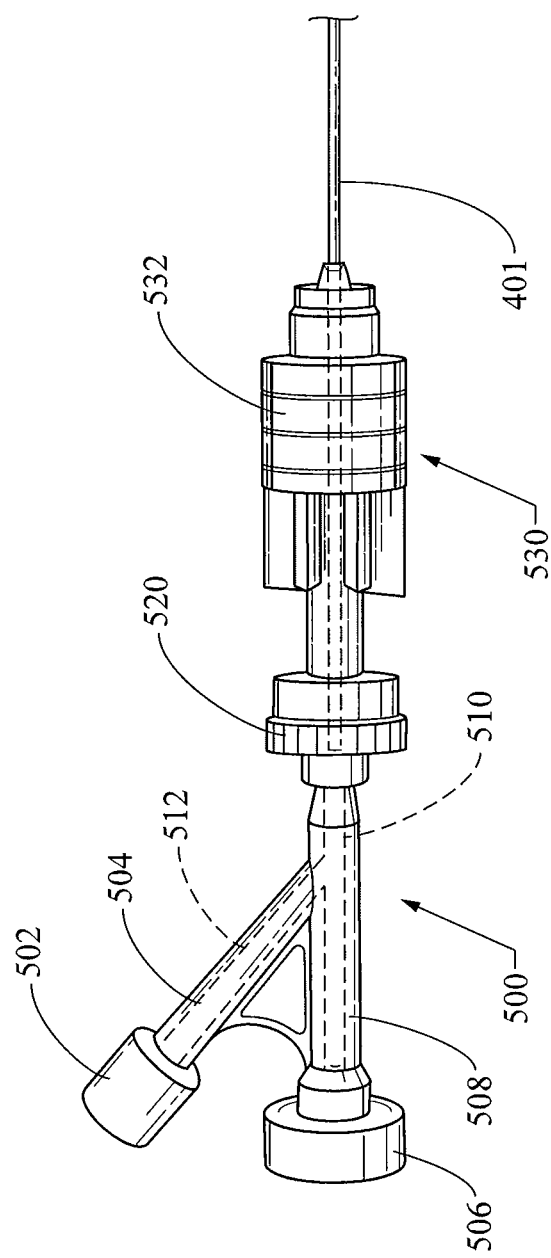
FIG. 9 depicts a detachable manifold configured for use with the valve of FIG. 1.

FIG. 9 shows balloon catheter 400 having a removable hub, embodied as a manifold 500, releasably attached to catheter shaft 401. The manifold includes a Luer-type connector 502 on a side branch 504 and another connector 506 on a linear branch 508 that is substantially coaxial with the longitudinal axis of catheter shaft 401. Manifold 500 includes a main lumen 510 that is in fluid communication with a lumen 512 of the side branch 504. Manifold 500 may be releasably attached to the catheter shaft by a Tuohy-Borst seal 520, or some other type of fluid-tight compression seal. The portion of catheter shaft containing valve 100 within lumen 402 can be aligned with seal 520 such that the seal can be tightened around catheter shaft 401 to engage valve 100. The valve can be opened by compressing the catheter shaft with the Tuohy-Borst seal until the catheter inner lumen surface 404 engages segment 110, causing deformation thereof and opening of portion 124 of lumen 120, such as depicted in FIGS. 7-8.

In some embodiments, manifold 500 may include a plurality of seals configured to engage the catheter shaft. For example, the manifold may include a fluid-tight compression seal 530 including a sliding member 532 that enforces a compression fit when in the distal position shown, and that releases the catheter shaft when retracted proximally. The Tuohy-Borst seal 520 may be dedicated to opening and closing valve 100. Thus, the manifold may be attached to the catheter body with the compression tight seal 530, and valve 100 may be opened and closed as needed with the Tuohy-Borst seal 520.

Figure 10A:
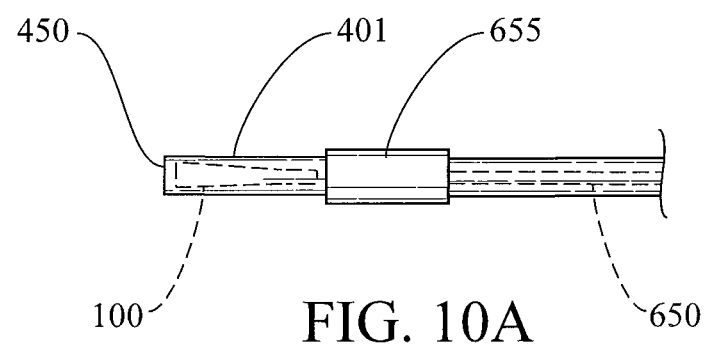
FIGS. 10A-10B depict a balloon catheter configured for use with the valve of FIG. 1.

A proximal end 450 of the catheter shaft 401 is shown in the side view of FIG. 10A. The catheter shaft may include a stiffening wire 650 embedded in its wall some distance distal of the absolute proximal end, and preferably distal from the location along the shaft where valve 100 will reside in lumen 402. A cannula 655 may bridge the "wired" and "non-wired" catheter regions, with the cannula preferably distal the location along the shaft where valve 100 will reside in lumen 402.

Figure 10B:
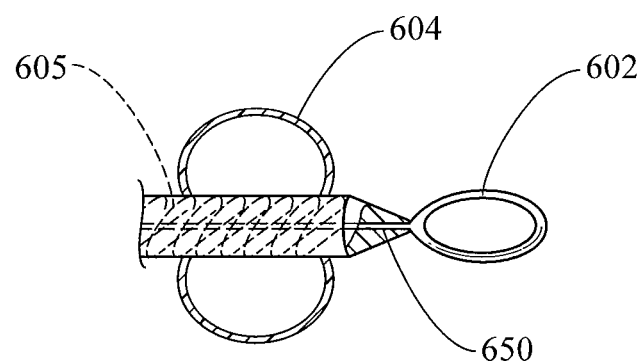

FIG. 10B shows a side view of the distal portion of balloon catheter 400. The balloon 604 is shown around the distal body portion of catheter shaft 401. A generally helical metal coil 605 may be disposed in the catheter in this distal portion to provide structural strength for navigating the catheter and to reinforce the catheter body in a region where one or more apertures (not shown) are included to provide a path of fluid communication from the catheter lumen 402 into the balloon lumen. The loop-tip 602 is attached to stiffening wire 650, and in the illustrated embodiment is sealed with the catheter shaft 401 by a general frustoconical adhesive or polymer structure that also seals the distal end of catheter inflation lumen 402. Loop-tip 602 preferably provides a generally atraumatic distal end that will facilitate navigation through body lumens and also permit monorail-style navigation along a wire guide.

Figure 11:
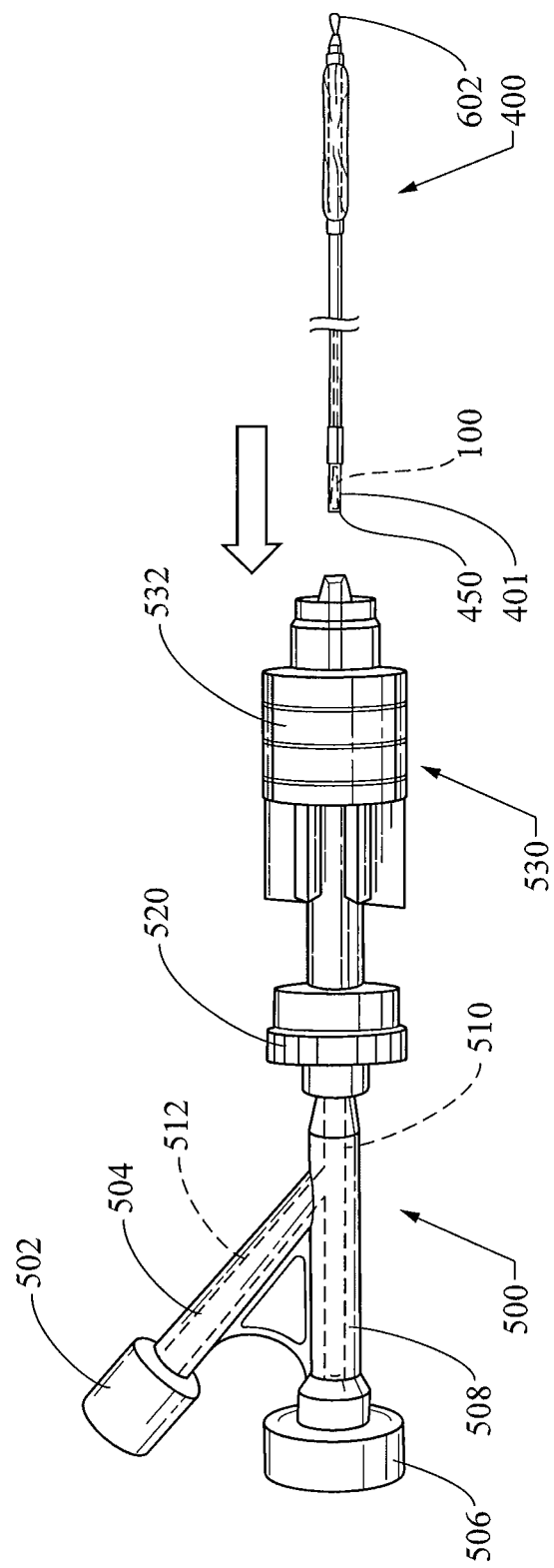
FIGS. 11-19 depict a cholangioscopy and biopsy procedure including a scope exchange using an anchoring balloon catheter with a removable hub.
Figure 12:
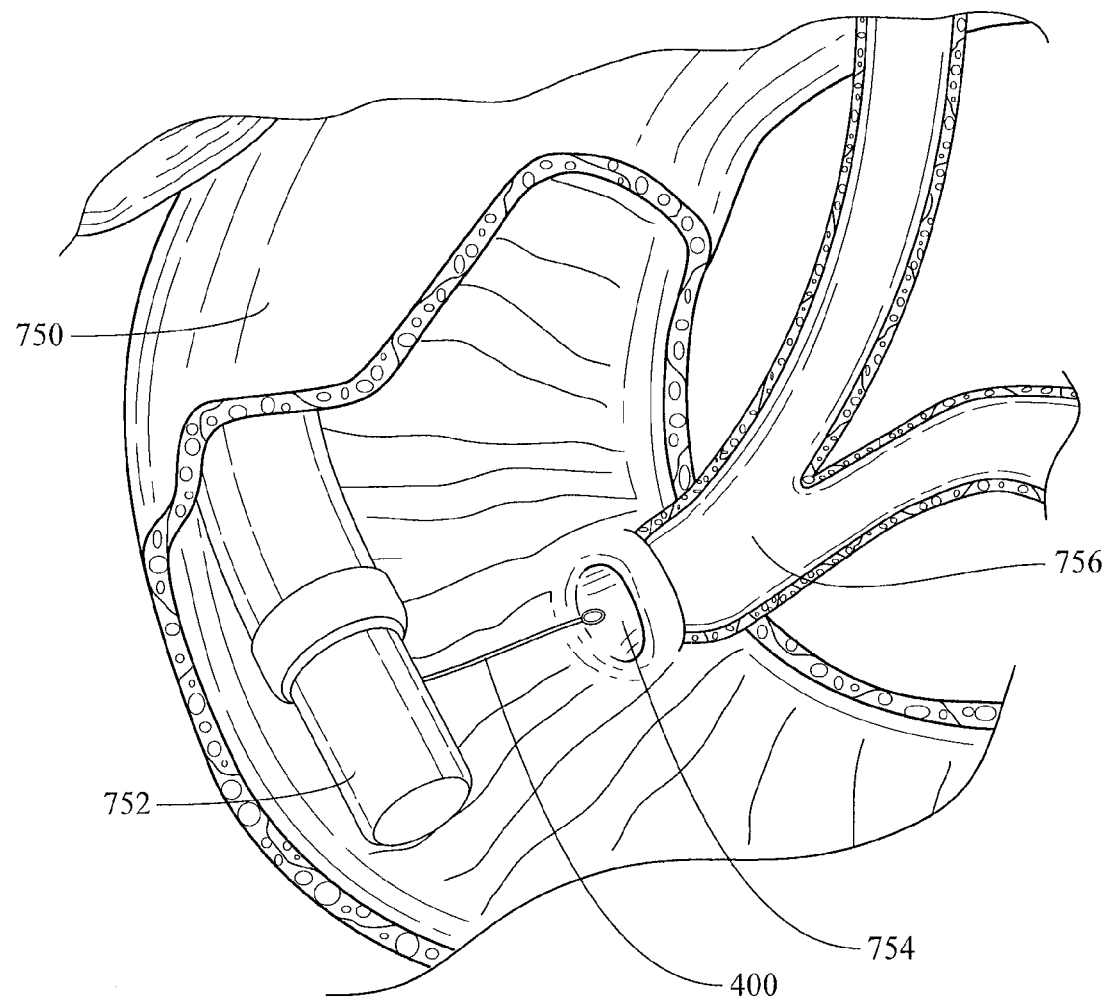

In one embodiment, the valve may be used with a balloon catheter to facilitate a scope exchange during a cholangioscopy procedure. Initially, the valve may be disposed in lumen 402 at proximal end 450 of catheter shaft 401, as depicted in FIG. 10A. Next, catheter shaft 401 may be inserted into and secured with manifold 500 as depicted in FIG. 11. The catheter shaft preferably is placed in the manifold such that Tuohy-Borst seal 520 aligns with valve 100, particularly segment 110. Next, as shown in FIG. 12, a side-viewing endoscope embodied as a duodenoscope 752 may be directed into the duodenum 750 of a patient adjacent the Amupulla of Vater about the Sphincter of Oddi 754, which is shown as having been cannulated (e.g., through a sphincterotomy). Loop-tipped catheter 400 extending through a working channel of duodenoscope 752 may then be directed through cannulated sphincter 754 into the common bile duct 756.

Figure 13:
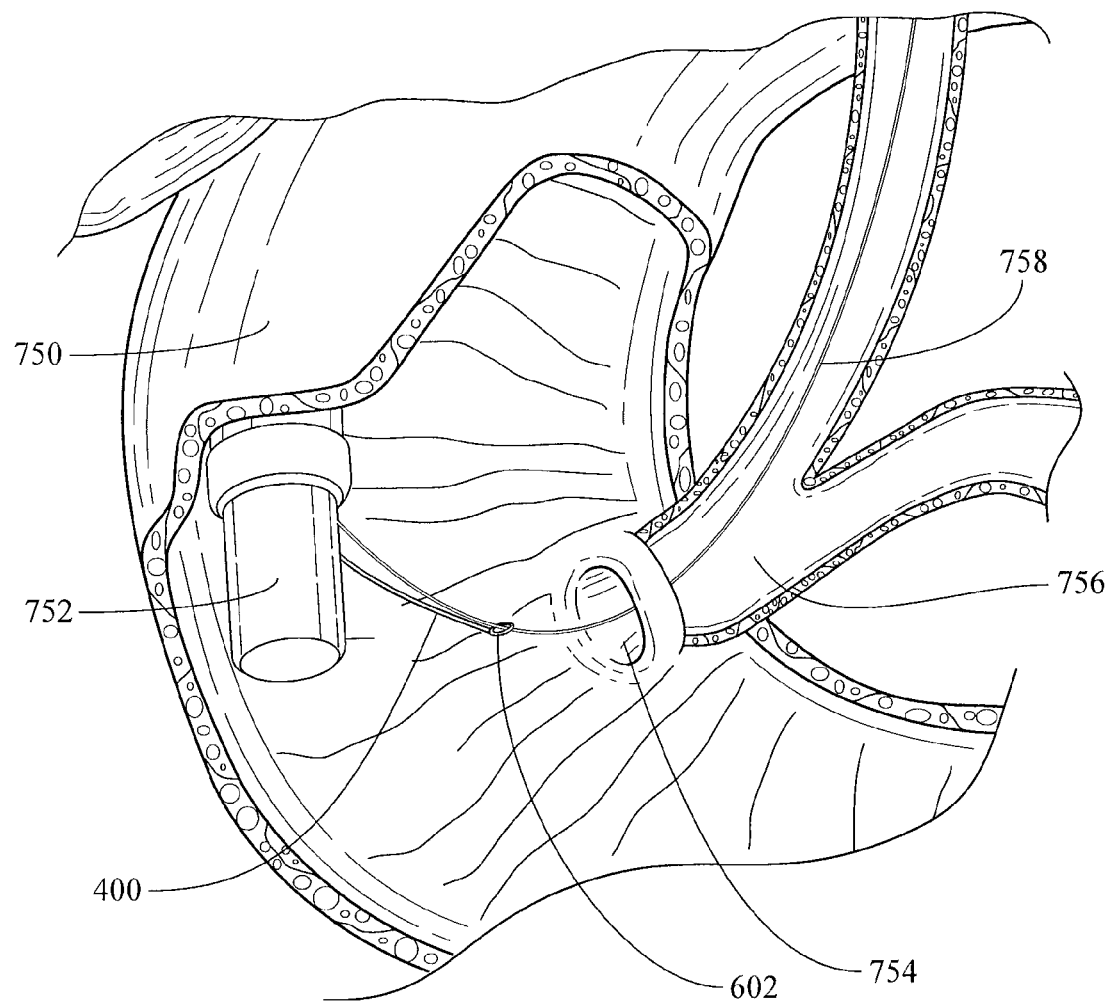

FIG. 13 shows an alternative method for introducing loop-tipped catheter 400 through the cannulated sphincter 754 into common bile duct 756 using a wire guide 758. In this embodiment, wire guide 758 is first navigated into common bile duct 756. Then, loop 602 of catheter 400 is looped around wire guide 758 and directed in monorail fashion therealong into the common bile duct.

Figure 14:
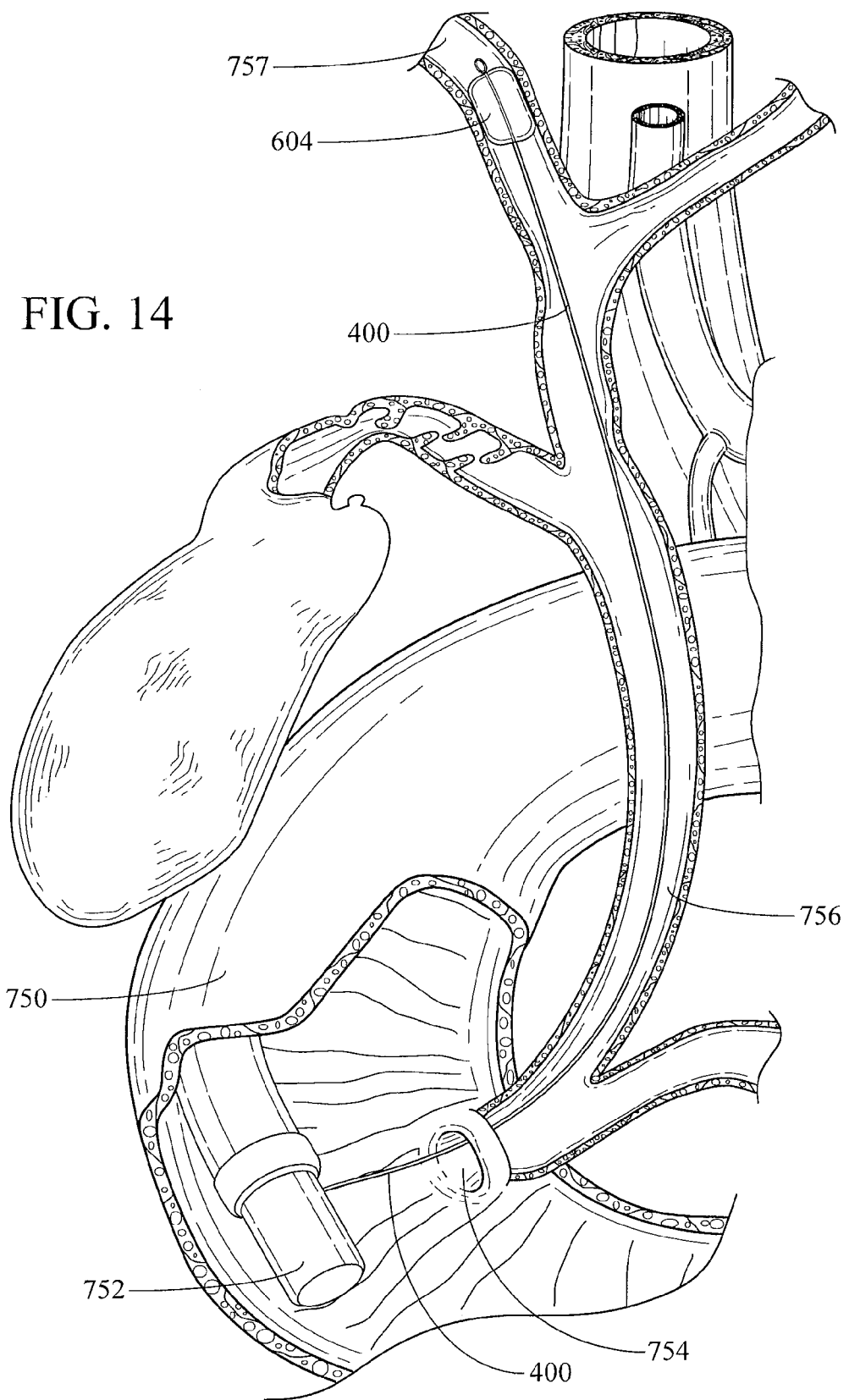

Regardless of which method is used to direct catheter 400 into the common bile duct, catheter 400 may be directed further into the hepatic branch side (or the pancreatic duct side) of common bile duct 756. Then, as shown in FIG. 14, balloon 604, which preferably will be a compliant balloon, may be inflated to anchor the distal end of the catheter in the hepatic branch 757. To inflate the balloon, with reference now to FIGS. 6-9, Tuohy-Borst seal 520 may be operated to engage and compress catheter shaft 401 until inner lumen surface 404 engages valve 100 at segment 110, causing elastic deformation thereof and opening of the valve to allow fluid communication through lumen 120. Once the valve is open as desired, a selected inflation media may be introduced through the valve and thereafter through inflation lumen 402 to inflate balloon 604. It is preferable that balloon 604 be inflated sufficiently to anchor catheter 400, but that it does not significantly distend the ductal surface contacted by the inflated exterior balloon surface. Compliant balloons may be made of latex or other biocompatible material having desirable elasticity. In some embodiments, a balloon may be non-compliant in accords with desirable manipulation during a surgical procedure.

Figure 15:
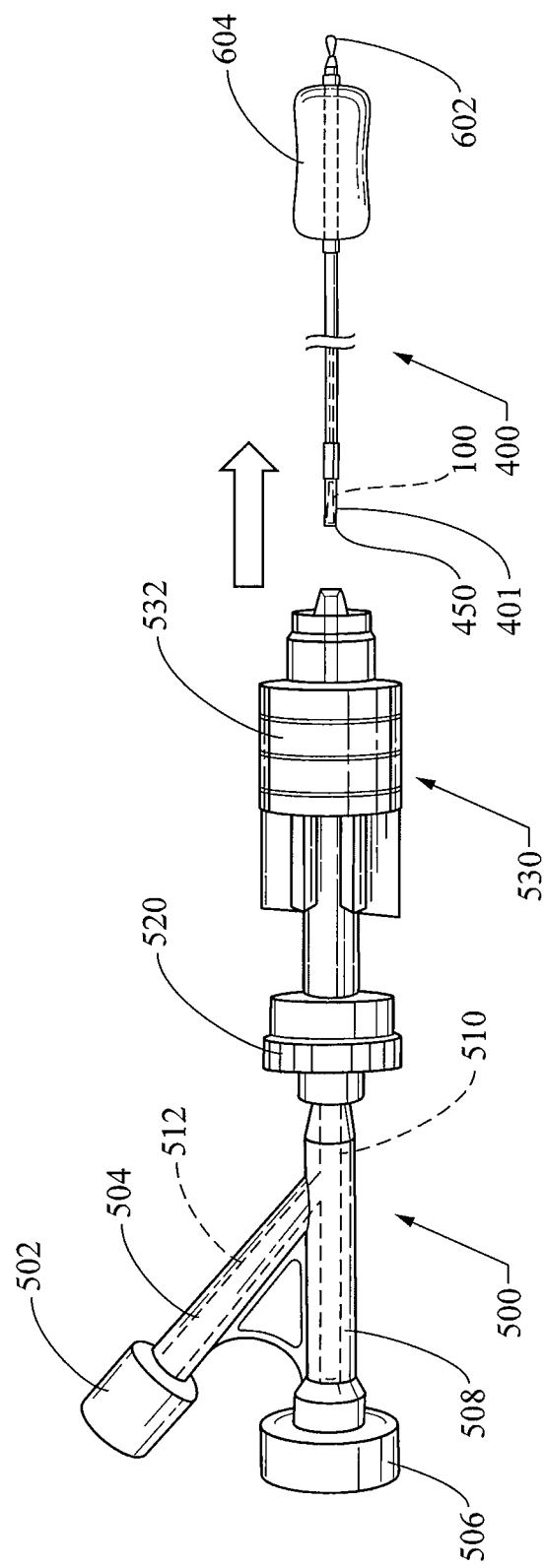
Figure 16:
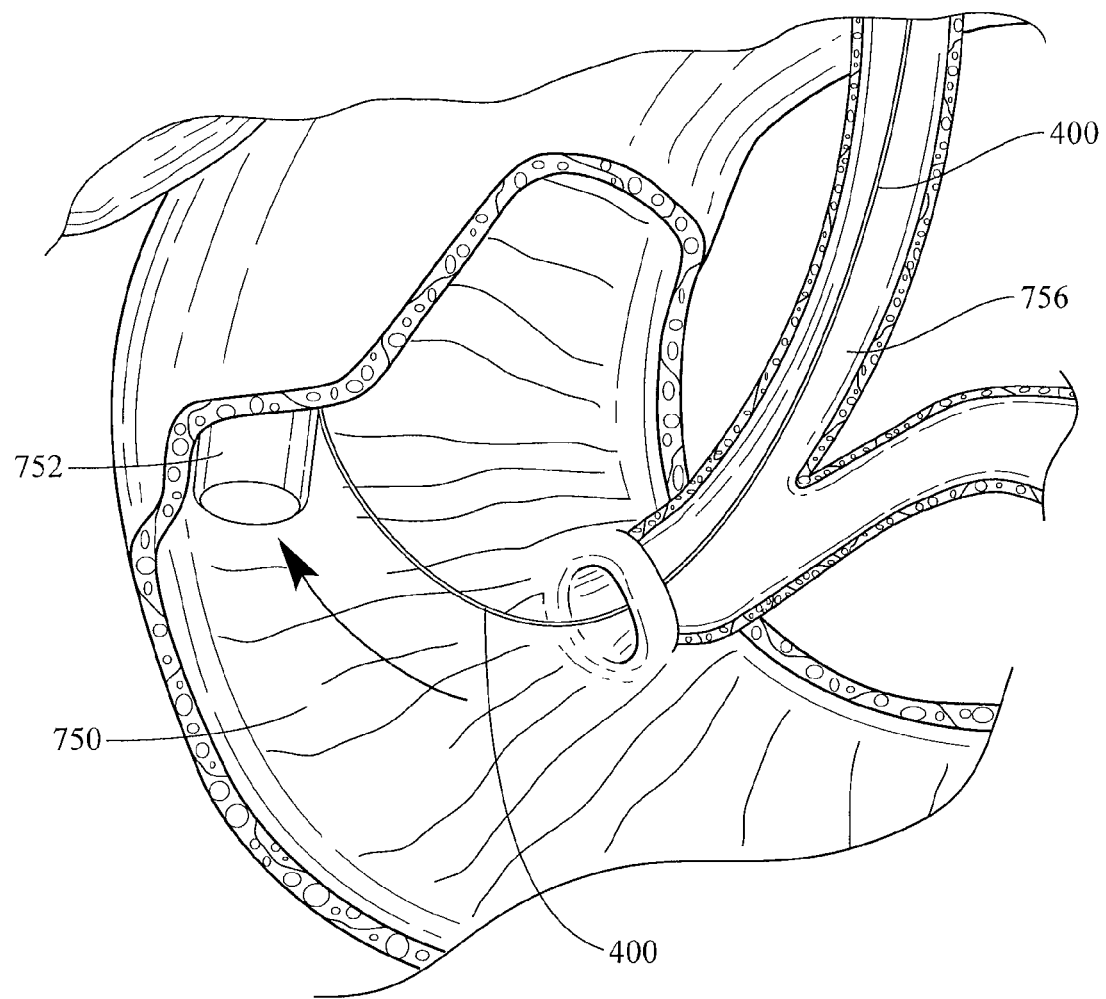

FIG. 15 shows the proximal end of balloon catheter 400, with manifold 500 being detached therefrom. Prior to detachment of manifold 500, valve 100 may be closed by disengaging Touhy-Borst seal 520, thereby sealing the proximal end of balloon catheter 400 to maintain fluid pressure in balloon 604. As will be appreciated with reference to FIG. 16, this removal of proximal manifold 500 allows a user to withdraw duodenoscope 752 over catheter shaft 401 while catheter 400 remains in place, anchored by the balloon (as shown in FIG. 14).

Figure 17:
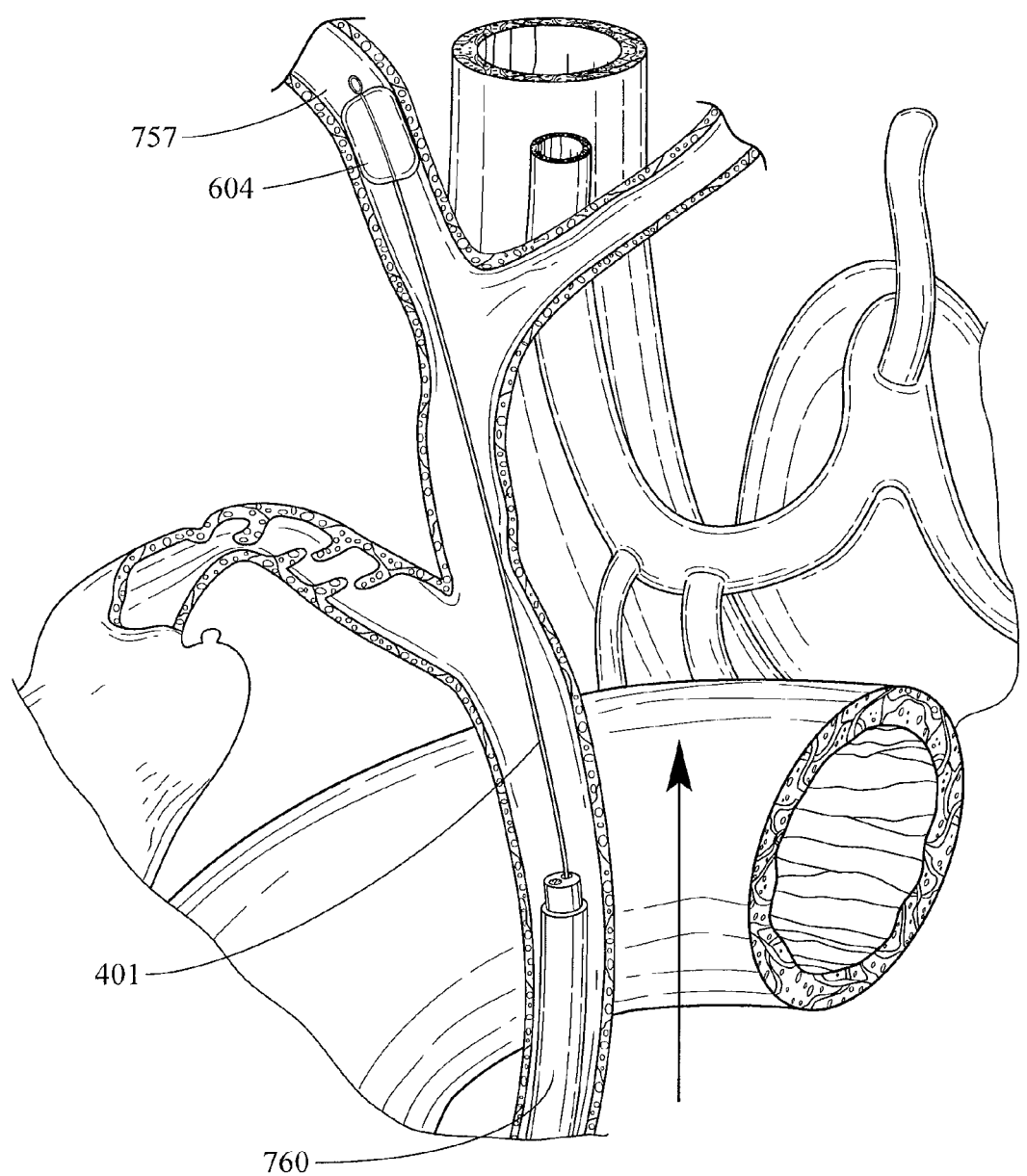
Figure 18:
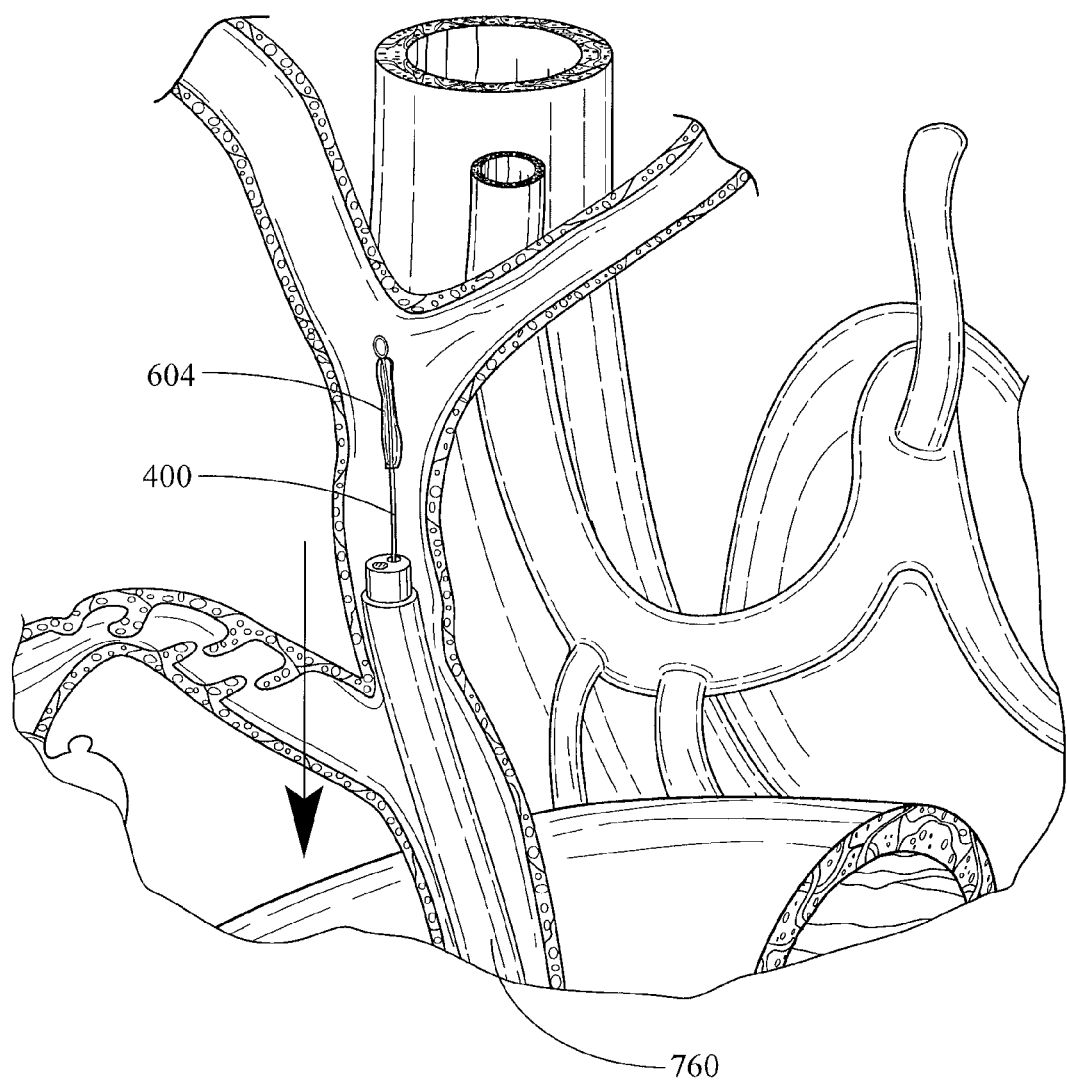
Figure 19:
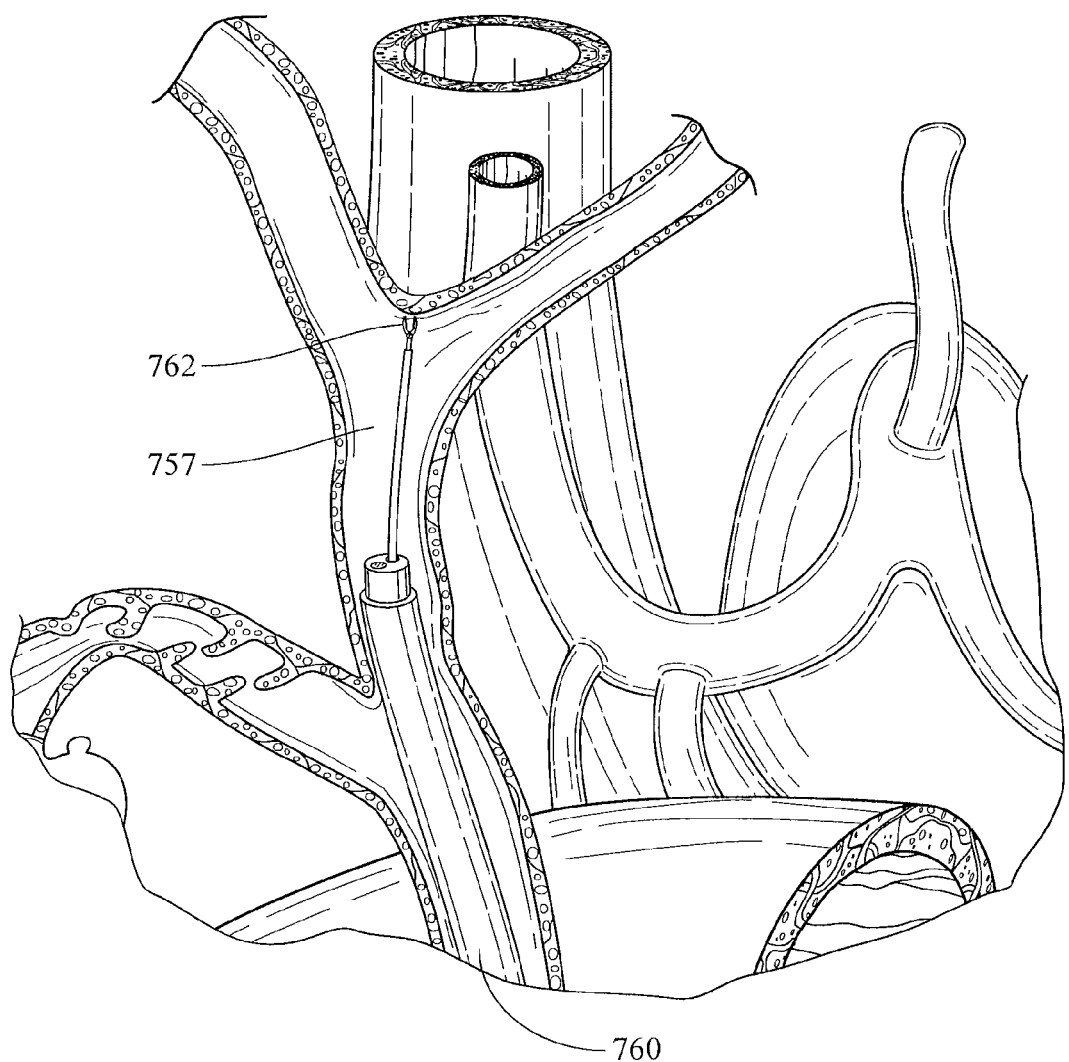

Next, an ultra-slim endoscope 760 is directed distally along catheter shaft 401. Specifically, proximal catheter end 450 is inserted into the distal end of an accessory/working channel of ultra-slim scope 760. As shown in FIG. 17, catheter shaft 401 may serve as a guide, allowing the distal end of ultra-slim scope 760 to be directed into common bile duct 756. Thereafter, as shown in FIG. 18, balloon 604 may be deflated by opening valve 100 and allowing the inflation media to escape, with the option of providing negative pressure to withdraw the media using a syringe or vacuum source. Catheter 400 may then be withdrawn, freeing up the accessory channel of ultra-slim scope 760. A user may then introduce a diagnostic or therapeutic instrument through the accessory channel of ultra-slim scope 760 such as, for example, biopsy forceps 762 as shown in FIG. 19.

Valve 100 may be manufactured by conventional techniques as is known in the art. In one exemplary embodiment, the valve may be manufactured by a primary process, such as injection molding. A secondary process may then be used to form portion 124 of lumen 120. The injection molding process includes filling a mold cavity with the selected material, applying heat and pressure, and cooling the manufactured article below its melt temperature upon release. Second portion 124 may be manufactured, for example, by cutting through segment 110 with a blade as appropriate to create a collapsed lumen (e.g., a slit) of desired dimensions.

The valve preferably is constructed of an elastically deformable material. Suitable materials include, but are not limited to, silicone rubbers, latex rubbers, polyurethanes, acrylic polymers, thermoplastic elastomers, or any materials or combination of materials similar to these in structure and function, provided said material(s) will affect a suitable seal and will elastically deform in the circumstances described.

While various embodiments of the presently disclosed valve have been described, it will be apparent to those of ordinary skill in the art that many more embodiments and implementations are possible within the scope of the present disclosure. Accordingly, the disclosure is not to be restricted except in light of the attached claims and their equivalents.

The invention claimed is:

1. An elongate medical device, comprising:
   a catheter comprising an elongate shaft extending between a proximal end and a distal end, the shaft comprising a shaft lumen there through;
   a valve body disposed within the shaft lumen, the valve body having a first segment and a second segment, the first segment integral with the second segment, wherein the first segment forms a seal with an inner surface of the shaft lumen, and wherein the second segment is elastically deformable from an elastically relaxed first configuration to a second configuration;
   a lumen extending through the valve body, the lumen in communication with the shaft lumen and having a first portion extending through the first segment and a second portion extending through the second segment, wherein the second portion is actuable between a closed configuration and an open configuration, wherein elastic deformation from the first configuration to the second configuration causes the second portion to actuate from the closed configuration to the open configuration, and wherein the elastic deformation from the first configuration to the second configuration is caused by an external force applied to an exterior surface of the catheter shaft, the external force being configured to cause simultaneous deformation of the catheter shaft and the valve body while maintaining the seal there between; and
   a hub disposed about the proximal end of the catheter shaft, the hub being configured to apply the external force to the exterior surface of the catheter shaft to cause simultaneous deformation of the catheter shaft and the valve body, wherein the hub is removable from the catheter shaft to reduce the profile of the elongate medical device.

2. The elongate medical device of claim 1 wherein the second segment has an elliptic cross section in the first configuration and a substantially circular cross section in the second configuration.

3. The elongate medical device of claim 2 wherein the first segment has a proximal end having a circular cross section and a distal end having an elliptic cross section.

4. The elongate medical device of claim 1 wherein the valve body comprises at least one material selected from the group consisting of silicone rubbers, latex rubbers, polyurethanes, acrylic polymers, and thermoplastic elastomers.

5. The elongate medical device of claim 1 wherein the elongate medical device is a balloon catheter and the shaft lumen is an inflation lumen.

6. The elongate medical device of claim 1 wherein the second segment in the first configuration has a transverse diameter ranging from about 0.5 mm to about 3.5 mm, and a conjugate diameter ranging from about 0.25 mm to about 3.5 mm.

7. The elongate medical device of claim 1 wherein the second portion of the lumen is a slit when in the closed configuration, wherein elastic deformation of the second segment from the first configuration to the second configuration causes the slit to actuate to the open configuration.

8. The elongate medical device of claim 1 wherein the second segment has an elliptic cylinder shaped body in the first configuration.

9. The elongate medical device of claim 1 wherein the first segment has a frustum cylinder shaped body.

10. An elongate medical device, comprising:
    a catheter comprising an elongate shaft extending between a proximal end and a distal end, the proximal end of the shaft being elastically deformable, the shaft comprising a shaft lumen extending there through;
    an elastically deformable valve body disposed within the shaft lumen at the proximal end of the shaft, the valve body extending from a proximal end to a distal end along a longitudinal axis;
    a slit extending through at least a portion of the valve body along the longitudinal axis, the valve body having a first radial axis corresponding to the slit, wherein compression of the valve body along the first radial axis causes elastic deformation of the valve body and causes the slit to open to provide a path of fluid communication through the valve body from the proximal end to the distal end; and
    a detachable hub operably coupled to the proximal end of the catheter shaft, the detachable hub comprising a means for applying an external force to an exterior surface of the proximal end of the catheter shaft so as to cause simultaneous deformation of the catheter shaft and the valve body along the first radial axis.

11. The elongate medical device of claim 10 wherein the valve body is one of an elliptic cylinder shaped body or a cylindrical shaped body.

12. The elongate medical device of claim 10 wherein the valve further comprises a seal portion proximal to and integral with the valve body, the seal portion having a lumen extending longitudinally therethrough and aligned with the slit, wherein the seal portion is configured to engage and form a fluid tight seal with an interior surface of the shaft lumen of the medical device.

13. The elongate medical device of claim 12 wherein the seal portion is a frustum shaped body having a circular cross section that tapers to an elliptic cross section from a seal portion proximal end to a seal portion distal end.

14. A balloon catheter assembly, comprising:
    a balloon catheter having a proximal end, a distal end, a first lumen extending from the proximal end to the distal end, and a balloon disposed on the distal end and in fluid communication with the first lumen;
    a valve comprising a valve body disposed within the first lumen at the proximal end of the balloon catheter, the valve body having a collapsed second lumen extending therethrough, wherein the second lumen can be opened by elastically deforming the valve body from a first configuration to a second configuration; and
    a detachable hub disposed about the proximal end of the balloon catheter and comprising a seal capable of elastically deforming the valve body by applying an external force to an exterior surface of the proximal end of the balloon catheter to open the second lumen.

15. The balloon catheter assembly of claim 14, wherein the seal is a Tuohy-Borst seal.

16. The balloon catheter assembly of claim 14 wherein the valve comprises a seal portion proximal to and integral with the valve body, the seal portion comprising a third lumen extending therethrough, wherein the second lumen and the third lumen are aligned and wherein the seal portion is configured to engage and form a fluid tight seal with an interior surface of the first lumen.

\* \* \* \* \*